United States Patent [19]

Clemens

[11] Patent Number: 5,727,570
[45] Date of Patent: Mar. 17, 1998

[54] METHOD OF TREATING HYPERLIPIDEMIA IN HUMANS

[76] Inventor: Anton H. Clemens, 5854 Schumann Dr., Madison, Wis. 53711

[21] Appl. No.: 749,333

[22] Filed: Nov. 14, 1996

[51] Int. Cl.$^6$ .................................................. A61B 19/00
[52] U.S. Cl. .............................................. 128/898; 604/49
[58] Field of Search ...................... 128/898; 604/890.1, 604/891.1, 892.1, 49; 424/473, 486, 467, 482, 485, 487, 488; 514/467, 120, 161, 195, 201–208

[56] References Cited

PUBLICATIONS

Sohel et al. "Influence of Aedrenergic Blockers and Antilipemic Agents on Pharmacodynamic Actions of Morphine in Carbon Tetrachloride–Treated Rats." Toxicol Appl Pharmacol 27(3): 477–483, Mar. 1974.

Stern et al. "Lack of Awareness and Treatment of yperlipidemia in Type II Diabetes in a Community Survey." JAMA 262(3): 360–4, Jul. 1989.

*Primary Examiner*—Vincent Millin
*Assistant Examiner*—Kelly O'Hara
*Attorney, Agent, or Firm*—John H. Engelmann

[57] ABSTRACT

A method of treatment of humans suffering from hyperlipidemia which comprises administering, by a pharmaceutically effective mode, a drug composition selected from the group consisting of opiate antagonists, and drugs which substantially equally reduce the amounts of catecholamines bound to all catecholamine binding sites, is disclosed.

20 Claims, No Drawings

METHOD OF TREATING HYPERLIPIDEMIA IN HUMANS

BACKGROUND OF THE INVENTION

Coronary heart disease is one of the major causes of death in the industrialized world. Hyperlipidemia has been recognized as one of primary risk factors, in particular elevated levels of total and low density lipoprotein cholesterol, elevated levels of triglycerides and low levels of high density lipoprotein cholesterol, as well as elevated levels of free fatty acids. State-of-the-art therapeutic regimens have failed to treat and correct the entire complex of hyperlipidemia with a single pharmaceutical agent. Drugs such as clofibrate/gemfibrozil lower triglycerides, by some unknown mechanism, but have no effect of the free fatty acid level, and no effect upon the total cholesterol level. However, the drugs may shift the proportion of cholesterol found in the form of low and high density lipoprotein cholesterol. In patients suffering from an elevated level of low density lipoprotein cholesterol, the drugs may actually increase the level of low density lipoprotein cholesterol. Drugs like lovastatin, on the other hand, lower the level of both total and low density lipoprotein cholesterol, while slightly increasing the level of high density lipoprotein cholesterol. However, these drugs have no effect on free fatty acids and little or no effect on triglyceride levels.

Lipid metabolism is rather complex. While it is clear that hyperlipidemia is associated with the development of coronary heart disease, there is no clear understanding of the pathogenic causes and pathways leading up to the manifestation of the various lipid disorders, nor is there any agreement as to the relative roles of lipid ingestion versus endogenous lipogenesis in the etiology of lipid abnormalities. Insulin resistance has, traditionally, been considered a state in which a normal amount of insulin produces a subnormal biological response, as is the case in non-insulin-dependent diabetics and/or in pre-diabetic subjects effected by glucose intolerance or impaired glucose tolerance. These subjects require (and endogenously produce) higher than normal levels of insulin to compensate for their insulin resistance to normalize their blood glucose levels. As a consequence, the traditional definition of insulin resistance was expressed in the Insulin/Glucose Ratio (I/G). It has only been recently that other biological functions of insulin have become the focus of more intense scientific interest, e.g. the role of insulin in endogenous lipogenesis. Although an interaction between obesity and insulin resistance has been established, the cause and effect relationship between these syndromes is still hotly debated in the scientific community: which comes first, insulin resistance or obesity or hyperlipidemia. Whatever the exact cause(s) of hyperlipidemia may be, current therapeutic modalities of lowering one or the other lipid fraction are not capable of correcting the entire hyperlipidemic complex at or close to its original cause.

During the investigations into, and development of, non-addictive morphine based analgesics, typically requiring a combination of agonistic and antagonistic actions at various opiate receptor sites, i.e. $\mu$, $\delta$ and $\kappa$ receptors, a variety of so-called 'pure' antagonists have evolved as by-products, and some of these narcotic antagonists, or anti-opioids, have been shown to have potential in the treatment of a variety of disease conditions.

U.S. Pat. No. 4,272,540 discloses various 14-methoxy substituted 3-hydroxy or 3-methoxy-6-one morphinans which are variously useful as analgesics, narcotic antagonists, and mixed analgesics and narcotic antagonists.

U.S. Pat. No. 4,451,470 discloses 14-fluoromorphinans which are useful as analgesic, narcotic antagonists and/or anorexigenic agents.

U.S. Pat. No. 4,478,840 discloses 17-cycloalkylmethyl-4,-5$\alpha$-epoxymorphinan-3,14-diol compounds useful for suppression of appetite in mammals.

U.S. Pat. No. 4,511,570 discloses a method of treating senile dementia which comprises periodic oral delivery of a pharmaceutically effective amount of 6-methylen-6-desoxy-N-cyclopropylmethyl-14-hydroxydihydronormorphone.

U.S. Pat. No. 4,619,936 discloses pharmaceutical compositions containing (5$\alpha$,6$\alpha$)7,8-didehydro-4,5-epoxy-17-(2-propanyl)-morphinano-3,6-diol for the purpose of appetite reduction.

U.S. Pat. No. 4,857,533 discloses a method of treating a human or animal patient suffering from an autoimmune disease which comprises the daily administration of the narcotic antagonists nalmefene or naltrexone.

U.S. Pat. No. 4,863,928 discloses a method of treating a human or animal patient suffering from an arthritic disease which comprises the daily administration of the narcotic antagonists nalmefene or naltrexone.

U.S. Pat. No. 4,877,791 discloses a method of treating a human or animal patient suffering from intestinal cystitis which comprises the daily administration of the narcotic antagonists nalmefene or naltrexone.

U.S. Pat. No. 4,880,813 discloses a method of treating patients suffering from allergic rhinitis which comprises the topical administration to the nasal passages of the narcotic antagonist nalmefene or a salt thereof.

U.S. Pat. No. 4,882,335 discloses a method useful as an adjunct in the treatment of alcoholism. The method involves having the patient drink alcoholic beverages while an opiate antagonist blocks the positive reinforcement effects of ethanol in the brain.

U.S. Pat. No. 4,994,466 discloses a method of treating a human or animal patient suffering from multiple sclerosis which comprises the daily administration to such patient of a pure narcotic antagonist, e.g., nalmefene or naltrexone.

U.S. Pat. No. 5,086,058 discloses a method for treating alcoholism. The method involves having the patient drink alcoholic beverages while nalmefene, an opiate. antagonist, blocks the positive reinforcement effects of ethanol in the brain.

U.S. Pat. No. 5,356,900 discloses a method of treating a human patient suffering from chronic herpes virus infections which comprises administration to such patient of an essentially pure narcotic antagonist exhibiting substantially higher blocking action against $\mu$ opiate receptor sites than against $\delta$ receptor sites.

Naltrexone, an antiopioid with unequal opioid receptor binding, by an order of magnitude, has been used in an attempt to reduce body weight, but with inconsistent results. (Atkinson et al, Clin. Pharmacol. Ther. 10/85:pp 419–422). This report has also raised questions about a potential hepatic toxicity of naltrexone in humans.

Elevated insulin levels have been reduced, for a period of a few days, in a select patient population of four women with polycystic ovary syndrome with Acanthosis Nigrians, by Nalmefene (6-desoxy-6methylene-naltrexone), an antiopioid with a structure and relative receptor binding characteristics similar to naltrexone, but of increased potency (J. R. Givens et al; J. Clin. Endocr. & Metab. 64/2, 1987, pp.377–382). This report covers concentrations of insulin and glucose, the Insulin Glucose Ratio (I/G) as a measure of insulin resistance, as well as growth hormone (GH), luteinizing hormone (LH), follicle stimulating hormone (FSH), dehydroepiandrosterone sulfate (DHEAS), cortisol, testosterone and prolactin (PRL) levels during the study. This report does, however, not report any values on blood lipids, i.e. free fatty acids (FFA), triglycerides (TG), and any of the cholesterol fractions.

Anti-opioids, or narcotic antagonists, are characterized by their ability to displace narcotic agonists from the respective receptors, and since narcotics, in general, possess several agonist actions, e.g. μ, δ, and κ, anti-opioids, typically, possess antagonist capabilities for those receptors as well. In general, the antagonist activity, or effectiveness of anti-opioids at the various receptor sites is not equal and may vary significantly, oftentimes by more than an order of magnitude. In such case, e.g. for naltrexone, the μ receptor binding effectiveness is 12 times higher than its effectiveness to bind to a κ receptor, which will result in a 12-fold increase of agonist displacement at the μ receptor over the κ receptor. Since the μ receptor is known to control (amongst others) euphoria, a suppression of this action 12-fold over any action controlled by κ, e.g. various metabolic functions, can, actually result in disphoria, if the antiopioid dosage has to be increased to achieve the desired effect at the κ site.

$IC_{50}$ is defined as the concentration of a compound at which 50% of the standard molecule is displaced from the target receptor. For each receptor there is a prototype ligand. To measure the $IC_{50}$ for given anti-opiod, one measures the concentration of the anti-opiod which will drive 50% of the prototype ligand from the target receptor. For the μ receptor the prototype ligand is DHM (dihydromorphine). For the δ receptor, the prototype ligand is DADLE (D-Ala+D-Leu-Enkephalin), and for the κ receptor, the prototype ligand is EKC (ethylketocyclazocine).

SUMMARY OF THE INVENTION

The present invention provides a method of treatment of humans suffering from hyperlipidemia which comprises administering, by a pharmaceutically effective mode, a drug selected from the group consisting of opiate antagonists, and drugs which substantially equally reduce the amounts of catecholamines bound at all catecholamine receptor sites.

DETAILED DESCRIPTION OF THE INVENTION

Hyperlidemia is a group of conditions characterized by the elevation of one or more of the following lipid materials: free fatty acids, triglycerides, total cholesterol, and low density lipoprotein cholesterol. Hyperlipidemia may also be associated with decreased high density lipoprotein cholesterol.

In one embodiment the invention involves the control of hyperlidemia through control of the amounts of catecholamines which are bound at catecholamine binding sites. I have discovered that hyperlipidemia in humans may be treated by the administration, in a pharmaceutically acceptable manner, of a drug which substantially equally reduces the amounts of catecholamines which are bound to all catecholamine binding sites. Such a drug may act by interfering with catecholamine synthesis, and thereby reducing the amounts of catecholamines which are available for binding. On the other hand, the drug may act to reduce binding by acting as a catecholamine antagonist at the catecholamine binding sites. Other methods of reducing binding include reduction of catecholamine stores, and enhanced catecholamine clearance.

A single drug which provides equal reduction of amounts of catecholamines bound to all catecholamine binding sites is the most desirable treatment method. However, if the reduction of the amounts of catecholamines bound at the different binding sites are substantially equal, that is the differerence between the various binding reductions is not greater than a factor of three, the method will still work. Accordingly, a drug which substantially equally reduces the amounts of catecholamines bound to all catecholamine binding sites is defined as a drug which provides reduction of the amounts of catecholamines bound to all catecholamine binding sites and the degree of reduction of the catecholamine binding for the different sites varies by a factor of three or less. The measurement of the degree of reduction of catecholamine binding may be achieved by using radioactive labeled catecholamine agonists or antagonists i.e. selective blockers, and measurement of the amount of radioactivity incorporated at the respective sites or released into solution.

I have found that the administration of a drug which substantially equally reduces the amounts of catecholamines bound to all catecholamine binding sites, lowers the levels of free fatty acids, triglycerides, total cholesterol, and low density lipoprotein cholesterol while increasing the level of high density lipoprotein cholesterol. Accordingly, in one aspect, this invention relates to a method of treating hyperlipidemia in humans by the administration, in a pharmaceutically acceptable manner, of a drug which substantially equally reduces the amounts of catecholamines bound to all catecholamine binding sites. This may be accomplished by a singular agent or by a combination of drugs which, working together, act to control catecholamine synthesis, or act as antagonists to control the binding of catecholamines. Mixtures of drugs may present problems in that rate of absorption, metabolism, and excretion of the individual components may vary. Thus, the mixture that has an ideal balance one hour after the dose is administered may have much poorer balance three hours later. The degree of variability may also differ from patient to patient. Nonetheless, combination drugs are known, It is possible to overcome these problems with the proper selection of catecholamine antagonists or supressors of catecholamine synthesis.

There are a variety of catecholamine agonists and antagonists which act upon various catecholamine receptors including α1, α2, β1, and β2. Some of these receptors have effects which counter balance the effects of other receptors. Often blocking one receptor with a suitable antagonist can cause, over time, compensatory changes in the responses of other receptors, so that a drug may be effective in the short term but not in the long term. On the other hand, a substantially equal reduction in the amount of all catecholamines bound at the various catecholamie binding sites does not trigger such compensatory mechanisms and provides for a treatment modality which has long term effectiveness.

All catecholamines, including epinephrine and norepinephrine may be substantially equally suppressed or reduced by inhibiting the enzyme tyrosine hydroxylase. A drug which accomplishes this inhibition is α-methyltyrosine (metyrosine). Metyrosine is a drug which has been used for some time to suppress the synthesis of catecholamines particularly in the in the treatment of pheochromocytoma, a disease characterized by excessive catecholamine release. Accordingly, in a more limited aspect, this invention relates to a method of treating hyperlipidemia in humans by the administration of metyrosine to such human patients. The drug may be administered by any pharmaceutically acceptable method. Simple oral administration has been found to be adequate at a dosage in the range of 1–5 mg/kg b.i.d.

EXAMPLE I

A 54 year old male insulin resistant subject was given 250 mg metyrosine twice daily. After 8 weeks of this treatment regimen, his fasting blood glucose level (BGL) had decreased by 10% from 121 to 110 mg/dl, insulin by 32% from 19 to 13 µU/ml, free fatty acids (FFA) by 23% from 742 to 575 µE/L, triglycerides (TG) by 31% from 208 to 144 mg/dl, total cholesterol (TCH) by 30% from 299 to 209 mg/dl, LDL by 24% from 176 to 134 mg/dl, and HDL by 34% from 41 to 27 mg/dl, with a resulting LDL/HDL ratio initially increasing from 4.3 to 5.0, both values being outside the normal range.

After another 6 weeks of the treatment regimen (a total of 14 weeks), LDL decreased further from 134 to 119 mg/dl, resulting in a total reduction of 32% from the beginning of the study, and HDL increased to 39 mg/dl resulting in an LDL/HDL ratio of 3.1, now well within the normal range of 1.0–4.0. There was a slight decrease in body weight at week 8. Four (4) weeks following the discontinuation of the treatment regimen, all values returned essentially to their pre-study levels (Table I).

TABLE I

|  | BGL mg/dl | Insulin µU/ml | FFA µE/ml | TG mg/dl | TCH mg/dl | LDL mg/dl | HDL mg/dl | LDL/ HDL |
|---|---|---|---|---|---|---|---|---|
| INITIAL LEVELS | 121 | 19 | 742 | 208 | 299 | 176 | 41 | 4.3 |
| 8 WEEKS | 110 | 13 | 575 | 144 | 209 | 134 | 27 | 5.0 |
| 14 WEEKS | — | — | — | — | — | 119 | 39 | 3.1 |
| 4 WEEKS AFTER DISC. | 122 | 15 | 747 | 211 | 254 | 189 | 37 | 5.1 |

In another embodiment, the invention relates to the treatment of hyperlipidemia by the administration, of drugs which act purely as narcotic antagonists, also referred to as opiate antagonists, or anti-opioids. The term opiod and opiate are equivalent, and are used interchangeably herein. These anti-opioids interact with the natural opiate receptors and thereby block the receptors from interacting with opiate drugs. This effect of blocking the action of opiate drugs extends not only to blocking the traditional opium alkaloid drugs, but to blocking the action of the endogenous beta-endorphins, dynorphins and enkephalins produced within the human body.

Hyperlipidemia may be treated by the administration of drugs with purely opiate antagonistic effects, such as naloxone, naltrexone, nalmefene or 17-cyclopropylmethyl-3-hydroxy-14-methoxy-8β-methylmorphinan-6-one hydrochloride (CHMMO) by a pharmaceutically acceptable method.

There are several types of opiate receptor sites and the opiate antagonists do not, generally, have an equipotent effect on all the different receptor sites. In evaluating opiate antagonists for use in the treatment of elevated blood lipid levels, their interaction with the µ, δ, and κ opiate receptors is most important. Opiate antagonists, such as naloxone and naltrexone, which exert their greatest effect upon the µ receptors, may be used to treat hyperlipidemia, but may have undesirable CNS side effects due to their differing levels of effectiveness against the µ, δ, and κ opiod receptors. Therefore, opioid antagonists which have approximately equal effects on the µ, δ, and κ receptors are preferred for the treatment of hyperlipidemia in humans. More specifically, it is preferred that the $IC_{50}$ for the µ, δ, κ opiate receptors be within a factor of 10 of each other, and most preferred that the $IC_{50}$'s differ by a factor of less than three.

The major advantage of having the $IC_{50}$ for the µ, δ, κ opiate receptors be within a small factor of each other is that by reducing total opioid binding to CNS opioid receptors µ, δ and κ in an approximately equal manner, imbalances and/or counter regulatory effects, at the opioid receptor levels, of the endogenous opioids endorphins, enkephalins and dynorphins will be avoided. As noted above, it is most preferred that the $IC_{50}$ levels for the µ, δ, κ opiate receptors should be within a factor of three of each other. Although a factor of ten difference in $IC_{50}$ levels for the µ, δ, κ opiate receptors will not lead to precisely equal binding at all opiate receptors, the mismatch in binding may be within tolerable limits to achieve a balanced improvement of all blood lipids and associated reduction in free fatty acids.

EXAMPLE II

A 56 year old insulin resistant male subject was given 17-cyclopropylmethyl-3-hydroxy-14-methoxy-8β-methylmorphinan-6-one hydrochloride (CHMMO), a pure opioid antagonist, in two daily doses of 18 mg each for the duration of one week, followed by 9 mg b.i.d. for another 4 weeks. Blood glucose dropped by 15% from 111 to 95 mg/dl during the first week and remained essentially at the same level for the duration of the study and, by the end of the study, after 5 weeks, insulin had fallen by about 50% from 14 to 6 µU/ml, FFA by 23% from 754 to 580 µE/L, TG by 42% from 229 to 133 mg/dl, Total Cholesterol by 21% from 234 to 185 mg/dl, LDL by 7% from 156 to 145 mg/dl, and HDL increased by 20% from 30 to 36 mg/dl, improving the LDL/HDL Ratio by 23% from 5.2 to 4.0 over the study duration of 5 weeks. There was also a slight weight loss at the end of the study. (Table II).

TABLE II

|  | BGL mg/dl | Insulin µU/ml | FFA µE/ml | TG mg/dl | TCH mg/dl | LDL mg/dl | HDL mg/dl | LDL/ HDL |
|---|---|---|---|---|---|---|---|---|
| INITIAL LEVELS | 111 | 14 | 754 | 229 | 234 | 156 | 30 | 5.2 |
| 5 WEEKS | 95 | 6 | 580 | 133 | 185 | 145 | 36 | 4.0 |

The receptor binding on µ, δ, and κ opioid receptors for Naloxone, Naltrexone, CHMMO, and Nalmefene are:

|  | $IC_{50}$ µ | $IC_{50}$ δ | $IC_{50}$ κ |
|---|---|---|---|
| Naloxone | $3.8 \times 10^{-9}$ M | $2.7 \times 10^{-8}$ M | $6.0 \times 10^{-8}$ M |
| Naltrexone | $1.0 \times 10^{-9}$ M | $1.0 \times 10^{-8}$ M | $1.2 \times 10^{-8}$ M |
| CHMMO | $5.0 \times 10^{-10}$ M | $8.0 \times 10^{-10}$ M | $9.5 \times 10^{-10}$ M |
| Nalmefene | $1.0 \times 10^{-9}$ M | $0.6 \times 10^{-8}$ M | $0.5 \times 10^{-8}$ M |

Although it is preferred to find the balanced $IC_{50}$ level's for the µ, δ, and κ receptors opiate receptors within a single molecule one should not preclude the possibility of the use of a mixture of opiate antagonists. Mixtures of molecules present problems in that rate of absorption, metabolism, and excretion of the individual components may vary. Thus, the mixture that has an ideal balance one hour after the dose is administered may have much poorer balance three hours later. The degree of variability may also differ from patient to patient. Nonetheless, combination drugs are known, It is possible to overcome these problems with the proper selection of opiate antagonists and produce a composition with opiate antagonist properties such that the $IC_{50}$ levels for the μ, δ, and κ opiate receptors are equal within a factor of 10, or most preferably within a factor of three.

A correlation between the structure of the opiate antagonist and the relative strength of receptor binding has not been established. However, it is clear that any opiate antagonist which has $IC_{50}$ level's for the μ, δ, and κ opiate receptors within a factor of 10 antagonist which has $IC_{50}$ level's for the μ, δ, and κ opiate receptors within a factor of 10 of each other, or most preferably within a factor of three, or combination of such opiate antagonists which together have $IC_{50}$ level's for the m, d, k opiate receptors within a factor of 10 or three, of each other, may be used in the preferred embodiment of present method in order to the expected beneficial results.

I claim:

1. A method of treatment of humans suffering from hyperlipidemia which comprises administering, by a pharmaceutically effective mode, a drug composition selected from the group consisting of opiate antagonists, and drugs which substantially equally reduce the amounts of catecholamines bound to all catecholamine binding sites.

2. A method according to claim 1 wherein the drug composition is a singular drug which substantially equally reduces the amounts of catecholamines bound to all catecholamine binding sites.

3. A method according to claim 2 wherein the drug composition is a combination of drugs which substantially equally reduce the amount of catecholamines bound to all catecholamine binding sites.

4. A method of treatment of humans suffering from hyperlipidemia according to claim 3, in which the hyperlipidemia is associated with elevated levels of free fatty acids, triglycerides, total and low density lipoprotein cholesterol and reduced levels of high density lipoprotein cholesterol.

5. A method of treating humans suffering from hyperlipidemia according to claim 2 wherein the drug composition comprises α-methyltyrosine.

6. A method of treatment of humans suffering from hyperlipidemia according to claim 2, in which the hyperlipidemia is associated with elevated levels of free fatty acids, triglycerides, total and low density lipoprotein cholesterol and reduced levels of high density lipoprotein cholesterol.

7. A method of treating humans suffering from hyperlipidemia according to claim 1 in which the drug composition is a composition with purely opiate antagonist properties.

8. A method of treating humans suffering from hyperlipidemia according to claim 1 in which the drug composition with purely opiate antagonist properties has $IC_{50}$ levels for the μ, δ, and κ opiate receptors equal within a factor of 10.

9. A method according to claim 8 in which the composition with purely opiate antagonist properties is a single molecule.

10. A method according to claim 8 in which the composition with purely opiate antagonist properties comprises a mixture of opiate antagonists.

11. A method of treatment of humans suffering from hyperlipidemia according to claim 8, in which the hyperlipidemia is associated with elevated levels of free fatty acids, triglycerides, total and low density lipoprotein cholesterol and reduced levels of high density lipoprotein cholesterol.

12. A method of treating humans suffering from hyperlipidemia according to claim 1 in which the drug composition with purely opiate antagonist properties has $IC_{50}$ levels for the μ, δ, and κ opiate receptors equal within a factor of three.

13. A method according to claim 12 in which the composition with purely opiate antagonist properties is a single molecule.

14. A method according to claim 12 in which the composition with purely opiate antagonist properties comprises a mixture of opiate antagonists.

15. A method of treatment of humans suffering from hyperlipidemia according to claim 12, in which the hyperlipidemia is associated with elevated levels of free fatty acids, triglycerides, total and low density lipoprotein cholesterol and reduced levels of high density lipoprotein cholesterol.

16. A method of treatment of humans suffering from hyperlipidemia according to claim 7, in which the hyperlipidemia is associated with elevated levels of free fatty acids, triglycerides, total and low density lipoprotein cholesterol and reduced levels of high density lipoprotein cholesterol.

17. A method of treatment of humans suffering from hyperlipidemia according to claim 1, in which the hyperlipidemia is associated with elevated levels of free fatty acids, triglycerides, total and low density lipoprotein cholesterol, and reduced levels of high density lipoprotein cholesterol.

18. A method of treatment of humans suffering from hyperlipidemia in association with insulin resistance, which comprises administering, by a pharmaceutically effective mode, a drug composition with purely opiate antagonistic properties.

19. A method according to claim 18, in which the drug composition with purely opiate antagonistic properties has $IC_{50}$ levels for the μ, δ and κ opiate receptors equal within a factor of 10.

20. A method according to claim 18, in which the drug composition with purely opiate antagonistic properties has $IC_{50}$ levels for the μ, δ and κ opiate receptors equal within a factor of three.

* * * * *